(12) United States Patent
Liu

(10) Patent No.: US 9,655,814 B2
(45) Date of Patent: May 23, 2017

(54) ENERGY PHYSIOTHERAPY CARE INSTRUMENT

(71) Applicant: SHENZHEN RUIJISI TECHNOLOGY LIMITED, Shenzhen (CN)

(72) Inventor: Yin Liu, Chongqing (CN)

(73) Assignee: SHENZHEN RUIJISI TECHNOLOGY LIMITED, Shenzhen (CN)

( * ) Notice: Subject to any disclaimer, the term of this patent is extended or adjusted under 35 U.S.C. 154(b) by 481 days.

(21) Appl. No.: 14/158,943

(22) Filed: Jan. 20, 2014

(65) Prior Publication Data
US 2015/0202434 A1 Jul. 23, 2015

(51) Int. Cl.
*A61N 1/18* (2006.01)
*A61H 99/00* (2006.01)
*A61H 23/02* (2006.01)
*A61F 7/00* (2006.01)
*A61F 7/02* (2006.01)

(52) U.S. Cl.
CPC ............ *A61H 99/00* (2013.01); *A61F 7/007* (2013.01); *A61H 23/02* (2013.01); *A61F 2007/0204* (2013.01); *A61H 2201/0157* (2013.01); *A61H 2201/0207* (2013.01); *A61H 2201/0228* (2013.01); *A61H 2201/10* (2013.01)

(58) Field of Classification Search
CPC .................... A61H 99/00; A61H 23/02; A61H 2201/0228; A61H 2201/0207; A61H 2201/10; A61H 2201/0157; A61F 7/00; A61F 7/007; A61F 2007/0204
See application file for complete search history.

(56) References Cited

U.S. PATENT DOCUMENTS

| | | | | |
|---|---|---|---|---|
| 2003/0163068 A1* | 8/2003 | Kang | ................. | A61H 23/0245 601/15 |
| 2006/0206040 A1* | 9/2006 | Greenberg | ............. | A61H 9/005 601/9 |
| 2009/0287195 A1* | 11/2009 | Altshuler | ............... | A61H 99/00 606/9 |
| 2010/0179455 A1* | 7/2010 | Nebrigic | ................ | A61B 18/18 601/15 |
| 2014/0227548 A1* | 8/2014 | Myrick | .................... | C06B 45/30 428/570 |

* cited by examiner

*Primary Examiner* — Quang D Thanh
(74) *Attorney, Agent, or Firm* — Li & Cai Intellectual Property (USA) Office

(57) ABSTRACT

Disclosed is an energy physiotherapy care instrument comprises a box-shaped body, a massage handle, a power-transmitting apparatus installed inside the massage handle, a control circuit board configured and fixed inside the box-shaped body to regulate the temperature of the power-transmitting apparatus, a power module to provide power to the control circuit board, a wire connecting between the power-transmitting apparatus and the control circuit board. The massage handle comprises a plastic casing and a massage head, for contacting the human body, mounted on the plastic casing and having a plurality of energy particles embedded inside. The instant disclosure provides power to the energy particles via a thermal conduction to introduce the energy particles into the deep layers of skin and then inside the human body. The instant disclosure has remarkable results, such as substantial healthcare, cell repair, and cell protection, as well as light and conveniently portable.

4 Claims, 2 Drawing Sheets

ENERGY PHYSIOTHERAPY CARE INSTRUMENT

BACKGROUND OF THE INVENTION

1. Field of the Invention

The instant disclosure relates to a physiotherapy care instrument; in particular, to an energy physiotherapy care instrument can improve the blood circulation, to prevent from aging and cancer, help to remove tumor, heal liver disease and asthma, adjust blood pressure, clean toxins in the human body, improve upon disorders in the nervous system, obesity and other diseases, reduce wrinkles, and provide therapy to the skin.

2. Description of Related Art

Currently, the typical physiotherapy care instrument can active blood near the surface of the skin merely via simple massage, but can not provide lots of health care for food and can not ease diseases. Thus, the current market is need of a physiotherapy care instrument which can provide substantial therapeutic care and ease diseases, especially providing care for deeper skin layers and cure for diseases regarding internal organs.

SUMMARY OF THE INVENTION

The instant disclosure provides an energy physiotherapy care instrument that realizes practical physiotherapy care via massage, power-transmitting and energy physiotherapy care, in order to improve upon the aforementioned problems regarding to prior arts.

To improve upon the above problems, the instant disclosure provides an energy physiotherapy care instrument comprises a box-shaped body, a massage handle, a power-transmitting apparatus installed in the massage handle, a control circuit board configured and fixed in the box-shaped body to regulate the temperature of the power-transmitting apparatus, a power module to provide power to the control circuit board, a wire connecting between the power-transmitting apparatus and the control circuit board, in which the massage handle comprises a plastic casing and a massage head to contact the human body, and the massage handle is fixed on the plastic casing and has a plurality of energy particles embedded therein.

The high energy particles are Germanium particles, water soluble Titanium particles, Tourmaline particles, anion, infrared penetrative particles, light stone particles, silver nanoparticles, active particles, volcanic rock, various kinds of minerals and vitamins, in which there are 72 kinds in total.

Moreover, a power switch, a start/pause switch and a button are included to regulate the temperature of the power-transmitting apparatus, all of which are configured on the control circuit board.

The massage head is made of one of the following: biological crystal, crystal glass, and glass. The energy particles are embedded inside the massage head and after that the massage head becomes biological crystal.

Compare to the prior arts, the instant disclosure transmits power to the energy particles via thermal conduction to introduce the energy particles into deep layers of the skin and then into the human body, to be more detailed, the power-transmitting device of the instant disclosure is a power-transmitting sheet made of energy silica gel and the power-transmitting device makes the energy particles penetrate human skin tissues of about 20 cm deep, in order to help the diffusion of materials, help the blood microcirculation which improves metabolism, stabilize oxygen supply in blood, activate blood cells, increase activities of body cells, and enhance immunity. Also, the instant disclosure can adjust abnormal potential of the human body, in more details, as the potential of the cancer cells dramatically arises, it can capture electrons of cancer cells to lower the potential, thus inhibit cancer from worsening. Furthermore, it can strengthen natural healing ability, improve physical condition, prevent aging, remove tumor, heal liver disease and asthma, adjust blood pressure, clean toxin in body, and heal nervous system disorders and other chronic diseases. Particularly, the power-transmitting apparatus is a power-transmitting sheet made of energy silicon, and the power-transmitting sheet of the instant disclosure helps to transmit power to the energy particles such that the energy particles can penetrate skin tissues of about 20 cm deep in order to kill cancer cells. The energy particles are processed based on a predetermined ratio and the nano-technology. The particles are dissolved into the power-transmitting apparatus made of energy silicon. The crystal (also named the biological crystal in the instant disclosure) contacts the human body, which helps the energy particles to penetrate into skin tissues of about 20 cm deep, in order to generate a large amount of energy that reacts with certain toxins to form products which are harmless or less harmful. Further, the instant disclosure has remarkable results, such as substantial therapeutic care, cell repair, and cell protection. Besides, the instant disclosure is light and convenient portable.

Additionally, a vibrating motor is configured in the massage handle to provide vibration, an audio module is configured on the control circuit board to store audio data, and a speaker is mounted on the upside of a switch of the instrument. Therefore, via the vibrating motor, the massage handle can provide vibration. Via the audio module and the speaker, the user can be comforted by music during the therapy.

For further understanding of the instant disclosure, reference is made to the following detailed description illustrating the embodiments and examples of the instant disclosure. The description is only for illustrating the instant disclosure, not for limiting the scope of the claim.

BRIEF DESCRIPTION OF THE DRAWINGS

Embodiments are illustrated by way of example and not by way of limitation in the figures of the accompanying drawings, in which like references indicate similar elements and in which.

DETAILED DESCRIPTION OF PREFERRED EMBODIMENTS

Figure 1:
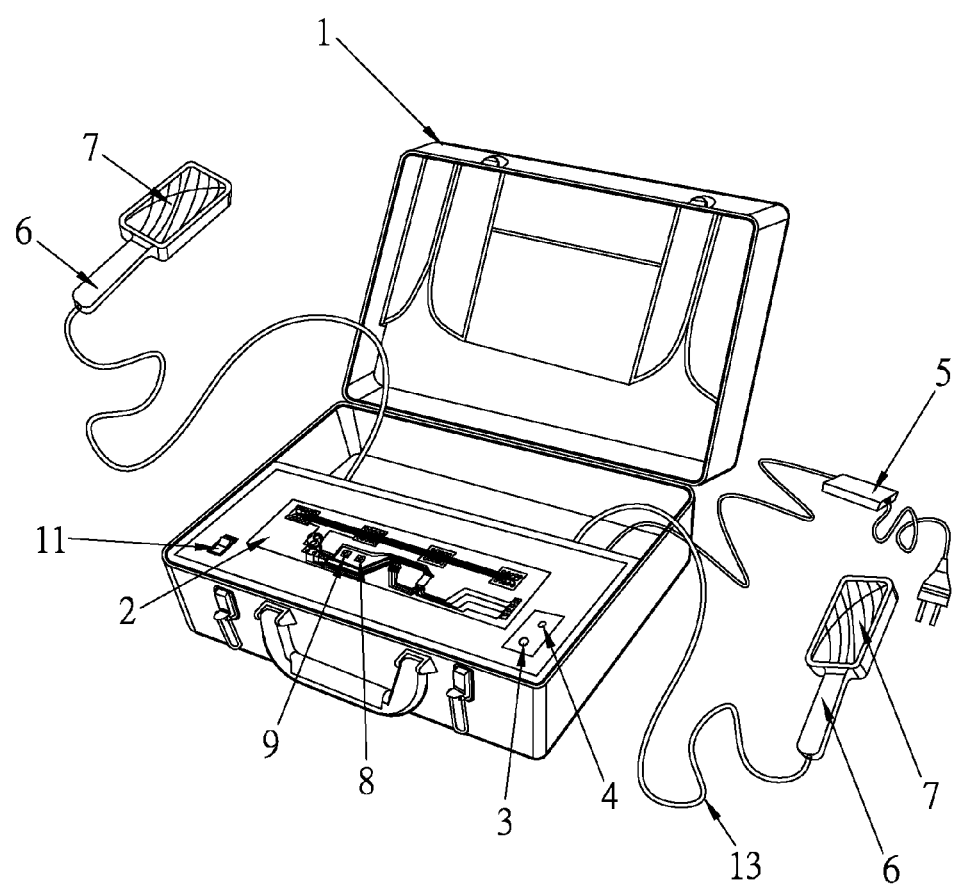
FIG. 1 shows a partial three-dimensional view along with a cross-section view according to a preferable embodiment of the instant disclosure.

The instant disclosure provides an energy physiotherapy care instrument. Please refer to FIG. 1 and FIG. 2. The energy physiotherapy care instrument comprises a box-shaped body 1, a massage handle 6, a power-transmitting apparatus installed and fixed inside the massage handle 6, a control circuit board 2 configured and fixed inside the box-shaped body 1 to regulate the temperature of the power-transmitting apparatus, a power module 5 to provide power to the control circuit board 2 (the power module transforms a voltage from 100-240V to 60V), and a wire 13 connecting between the power-transmitting apparatus and the control circuit board 2. The massage handle 6 comprises a plastic casing and a massage head 7 fixed on the plastic casing to contact the human body. The massage head 7 has a plurality of energy particles 12 embedded inside. The control circuit board 2 regulates the temperature of the power-transmitting apparatus such that the energy particles 12 of the massage head 7 become more active, and the energy particles 12 release energy into the deep layers of the skin and then inside the human body via thermal conductivity for the healthcare.

Preferably, the power-transmitting apparatus is a power-transmitting sheet made of energy silicon. The power-transmitting sheet of the instant disclosure helps to transmit power to the energy particles and facilitates the energy particles to penetrate into skin tissues of about 20 cm deep in order to kill cancer cells.

Also preferably, the energy particles 12 are Germanium particles, water soluble Titanium particles (also named liquid Titanium particles), Tourmaline particles (also named Tourmaline), anion, infrared penetrative particles, light stone particles, or silver nanoparticles. By mixing several kinds of particles based on a predetermined ratio and the nano-technology and dissolving the particles into the power-transmitting apparatus made of energy silicon, the crystal contacting the human body (also named the biological crystal in the instant disclosure) provides more preferable healing and healthcare. The energy particles 12 can adjust current in a body via the cell-ionization, and thus the flow of blood near surface of the skin is stimulated. As a result, the stimulated blood flow helps the human body to remove the reactants in blood, which are resulted from soreness. The energy particles 12 are introduced 14 cm deep inside the human body in order to kill harmful cells and to help the reproduction of new cells. Also, the energy particles 12 provide dehydrogenation and oxygen enrichment, thus helping the human body to maintain sufficient oxygen in order to maintain health. Particularly, the Germanium particles quicken the absorption of the anion (the particles with outer electrons) via the skin by the human body. Because of semi-conductivity, the Germanium particles are can active the skin. Additionally, if the Germanium ion enters the human body, it can be discharged along with harmful materials within 20 hours to 30 hours. Thus, there is no harm and no side-effect. If the Germanium ion contacts the human skin, it would enter the human skin due to semi-conductivity, and then penetrate into the capillaries within epidermal tissues. The Germanium ions, which flows in the bloodstream, cleans the blood and normalizing the blood in the bloodstream. Moreover, the Germanium ions can slow the dramatic flow of positrons to kill or ease the pain. Since titanium has the biocompatibility, thus can resist the erosion caused by the secretion. Besides, titanium is non-toxin which can be applied to any kind of sterilizing method.

Figure 2:
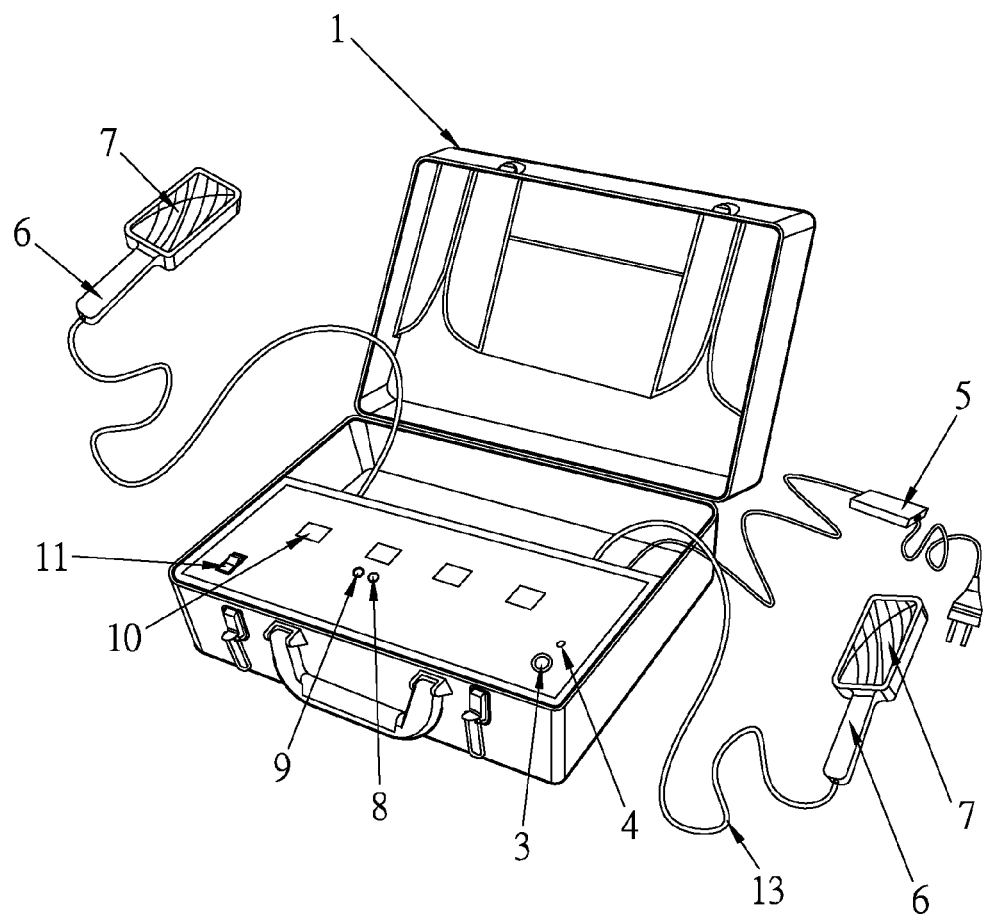
FIG. 2 shows a three-dimensional view according to a preferable embodiment of the instant disclosure.

Preferably, the control circuit board 2 is adapted to correspond to two massage handles 6. In FIG. 1, the cross-section view of the energy physiotherapy care instrument shows the control circuit board 2. The circuit board 2 includes a power switch 11, a start/pause switch 3, a working indicating light 4 and buttons 8 and 9 that are configured on the control circuit board 2 for regulating the temperature of the power-transmitting apparatus. Please refer to FIG. 2. Screens 10 for display are configured on the control circuit board 2, four of which are inline, from the left to the right to respectively show the actual temperature of the left massage handle, the set-up temperature, the working time, and the actual temperature of the right massage handle.

Figure 3:
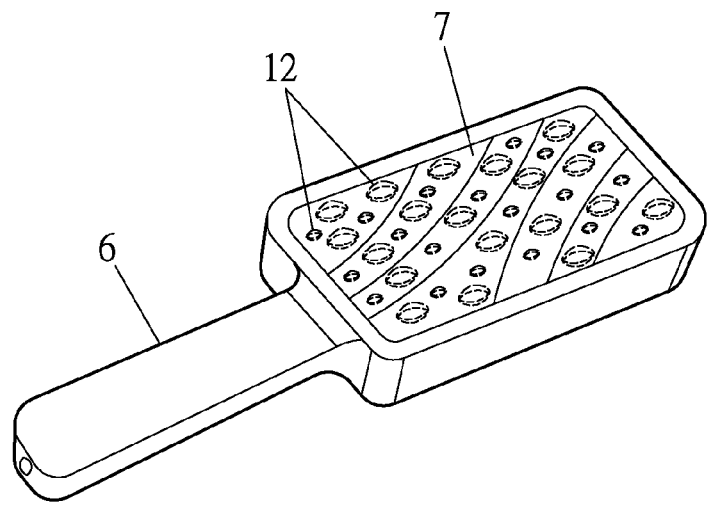
FIG. 3 shows a three-dimensional view illustrating a massage handle of an embodiment of the instant disclosure.

The massage head 7 is made of one of the following, biological crystal, energy crystal glass and energy glass. FIG. 3 shows a three-dimensional view of a massage handle 6 of an embodiment of the instant disclosure. FIG. 3 shows that the energy particles 12 are larger and embedded inside the massage head 7. In another embodiment of the instant disclosure, the energy particles 12 are smaller, which are added into the massage head 7 via water-solution or other methods.

Also preferably, a vibrating motor is configured inside the massage handle (7) to provide the vibration, an audio module is configured on the control circuit board (2) to store audio data, and a speaker is mounted on the upside of a switch of the instrument. Therefore, via the vibrating motor, the massage handle (7) can provide vibration, and via the audio module and the speaker, the user can be comforted by the music during the curing.

The aforementioned illustrations and following detailed descriptions are exemplary for the purpose of further explaining the scope of the instant disclosure. Other objectives and advantages related to the instant disclosure will be illustrated in the subsequent descriptions and appended drawings.

What is claimed is:

1. An energy physiotherapy care instrument, comprising:
a box-shaped body (1), a massage handle (6), a power-transmitting apparatus fixed in the massage handle (6), a control circuit board (2) fixed in the box-shaped body (1) to regulate temperatures of the power-transmitting apparatus, a power module (5) providing power to the control circuit board (2) and a wire (13) connected between the power-transmitting apparatus and the control circuit board (2);
wherein the massage handle (6) includes a plastic casing and a massage head (7) adapted to contact the human body, the massage head (7) is fixed on the plastic casing and has a plurality of energy particles (12) embedded therein.

2. The energy physiotherapy care instrument of claim 1, wherein the energy particles (12) are one chosen from the following: Germanium particles, water soluble Titanium particles, Tourmaline particles, anion, infrared penetrative particles, light stone particles, silver nanoparticles, active particles, and volcanic rock, and the energy particles (12) are processed via electrolytic nano technology; the power-transmitting apparatus is made of energy silicon.

3. The energy physiotherapy care instrument of claim 1, wherein the control circuit board (2) has a power switch, a start/pause switch, and a button configured thereon to regulate the temperature of the power-transmitting apparatus.

4. The energy physiotherapy care instrument of claim 1, wherein the massage head (7) is made of one chosen from the following: biological crystal, crystal glass, and glass.

* * * * *